United States Patent
Baldauf et al.

(10) Patent No.: US 6,536,262 B2
(45) Date of Patent: Mar. 25, 2003

(54) DETERMINATION OF THE ALCOHOL CONCENTRATION IN THE ELECTROLYTE OF FUEL CELLS

(75) Inventors: Manfred Baldauf, Erlangen (DE); Walter Preidel, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/105,850

(22) Filed: Mar. 25, 2002

(65) Prior Publication Data

US 2002/0121129 A1 Sep. 5, 2002

Related U.S. Application Data

(63) Continuation of application No. PCT/DE00/03168, filed on Sep. 12, 2000.

(30) Foreign Application Priority Data

Sep. 24, 1999 (DE) .......................... 199 45 931

(51) Int. Cl.[7] .............................. G01N 33/00
(52) U.S. Cl. .................................... 73/61.47
(58) Field of Search .................. 73/61.47, 53.04, 73/54.01–54.14, 54.17, 61.41, 63.43, 61.44, 61.64, 61.73, 61

(56) References Cited

U.S. PATENT DOCUMENTS 5,315,863 A    5/1994   Cowper
6,134,950 A   * 10/2000   Forster et al. ............. 73/54.01

FOREIGN PATENT DOCUMENTS

| DE | 1902481 | * | 8/1969 | ......... H01M/27/12 |
| JP | 60-114 557 | | 6/1985 | |
| SU | 1 789 909 A1 | | 1/1993 | |
| WO | WO 46869 A2 | * | 8/2000 | ........... H01M/8/00 |
| WO | WO 01/13451 A1 | | 2/2001 | |
| WO | WO 128021 A1 | * | 4/2001 | ........... H01M/8/04 |
| WO | WO 200128021 A | * | 7/2002 | ......... G01N/25/00 |

OTHER PUBLICATIONS

A.V. Wolf et al.: "Concentrative Properties of Aqueous Solutions: Conversion Tables", CRC Handbook of Chemistry and Physics, 69th ed., 1988–1989, CRC Press, Inc., Boca Raton, Florida, pp. D–219, D–238.

Agaev, N. et al.: "Experimental Determination of the Viscosity of Methyl Alcohol Aqueous Solutions at High Pressures and Different Temperatures", Chemical Abstract Service, Columbus, Ohio, XP–002 160 286.

Agaev, N. et al.: "Experimental Study of the Viscosity of Ethyl Alcohol Aqueous Solutions at High Pressures and Temperatures in the 0–30.deg. Range", Chemical Abstract Service, Columbus, Ohio, XP–002 160 287.

* cited by examiner

Primary Examiner—Hezron Williams
Assistant Examiner—Jay L Politzer
(74) Attorney, Agent, or Firm—Laurence A. Greenberg; Werner H. Stemer; Ralph E. Locher

(57) ABSTRACT

In a method for determining the alcohol concentration in the alcohol/water mixture of fuel cells that are operated with this mixture, in particular for direct methanol fuel cells, the alcohol/water mixture is pumped through a constriction. The differential pressure between the entry to and exit from the constriction and, if appropriate, the flow velocity of the mixture through the constriction are measured, and the alcohol concentration is determined therefrom.

8 Claims, 1 Drawing Sheet

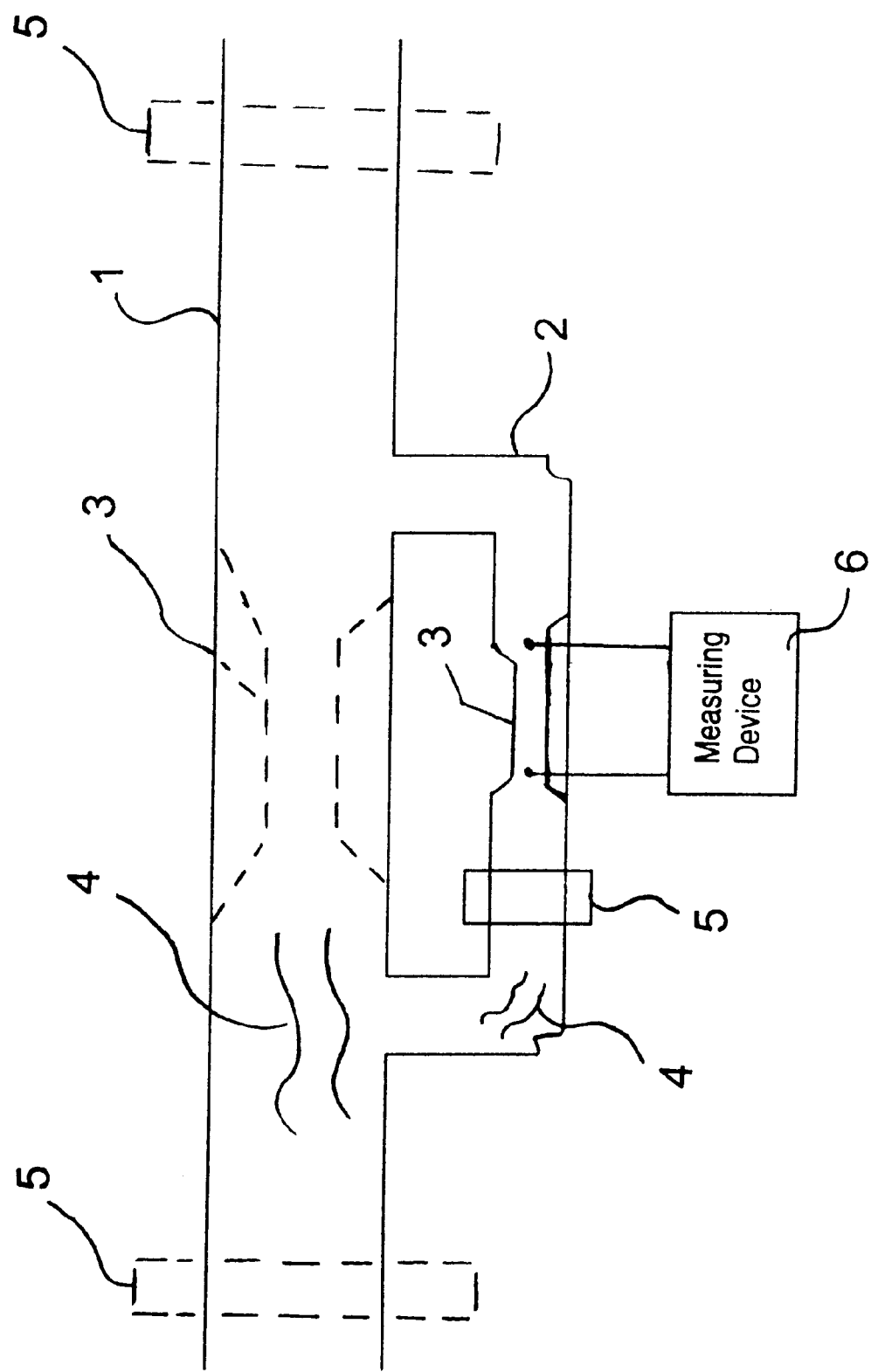

DETERMINATION OF THE ALCOHOL CONCENTRATION IN THE ELECTROLYTE OF FUEL CELLS

CROSS-REFERENCE TO RELATED APPLICATION

This application is a continuation of copending International Application No. PCT/DE00/03168, filed Sep. 12, 2000, which designated the United States.

BACKGROUND OF THE INVENTION

Field of the Invention

The invention relates to a method for determining an alcohol concentration in an alcohol/water mixture for fuel cells that are operated with this mixture, in particular direct methanol fuel cells. The invention also relates to an apparatus for carrying out the method.

To maintain the optimum operating parameters in fuel cells that are operated with liquid fuels, it is necessary to control the fuel concentration. For this purpose, the current concentration has to be determined.

Published, European Patent Application EP 0 684 469 A1 discloses a measuring unit for determining the concentration of low-molecular weight alcohols, such as methanol, in water or acids. The measuring unit has a porous anode for the electrochemical oxidation of the alcohol, a cathode for the electrochemical reduction of oxygen, an ion-conducting membrane disposed between the anode and the cathode and a diffusion-limiting membrane which is disposed on that side of the anode which is remote from the ion-conducting membrane. The measuring unit that, so to speak, represents a fuel cell is, for example, disposed in the fuel line and is held at a defined cell voltage by potentiostatic methods. Depending on the alcohol concentration, a current flows through the fuel cell, and the concentration can be worked out—by a calibration curve—from the level of the current. A procedure of this nature is relatively complex, since current and voltage have to be measured or monitored. In what are known as direct methanol fuel cells (DMFCs), the fuel methanol undergoes direct electrochemical oxidation, i.e. is reacted without the intermediate step of a reforming operation (see in this respect, for example, the reference by M. Waidhas in K. Ledjeff (Ed.) titled "Brennstoffzellen: Entwicklung, Technologie, Anwendung" [Fuel Cells: Development, Technology, Applications], C. F. Müller Verlag GmbH, Heidelberg 1995, pages 137 to 156). To achieve the optimum operating point in a DMFC, it is necessary to operate with a dilute fuel in excess.

For economic operation of a direct methanol fuel cell system (stack), it is necessary for the excess fuel and the water, which functions not only as a solvent but also as a reactant (anode reaction: $CH_3OH+H_2O \rightarrow CO_2+6\ H^++6\ e^-$) to be circulated. Therefore, the methanol/water mixture, after it leaves the stack (and after the carbon dioxide formed during oxidation of the methanol has been separated out) is fed back to the anode. Since a certain methanol concentration is required for operation of a DMFC-Stack, the methanol concentration in the anode cycle has to be measured, and, if the concentration is too low, the deficiency of fuel has to be metered in.

For on-line determination of the fuel concentration in the electrolyte of fuel cells, it has already been proposed in International Patent Disclosure WO 01/13451 A1, corresponding to U.S. patent application Ser. No. 10/078,123, to determine the dielectric constant of the mixture by measuring the frequency-dependent capacitance of a measurement cell through which the fuel/electrolyte mixture flows, the dielectric constant being dependent on the fuel concentration. This requires accurate monitoring of pressure and temperature, and the measuring unit must operate highly accurately. Moreover, this type of fuel determination is extremely sensitive to carbon dioxide that is dissolved in the electrolyte and is always present, for example, in the anode circuit of a DMFC-Stack that is operated with liquid fuel.

SUMMARY OF THE INVENTION

It is accordingly an object of the invention to provide a method and apparatus for determining an alcohol concentration in an alcohol/water mixture for fuel cells which overcome the above-mentioned disadvantages of the prior art methods and devices of this general type. Above all, it is necessary for it to be possible for the concentration determination to take place continuously and in parallel with the operation of the fuel cells or of the stack and for carbon dioxide present in the electrolyte not to cause any disruption.

With the foregoing and other objects in view there is provided, in accordance with the invention, a method for determining an alcohol concentration in an alcohol/water mixture of fuel cells operated with the alcohol/water mixture. The method includes the steps of pumping the alcohol/water mixture through a constriction; measuring a differential pressure between an entry to and an exit from the constriction; and determining the alcohol concentration from the differential pressure.

According to the invention, this is achieved by the fact that the alcohol/water mixture is pumped through a constriction, the differential pressure between the entry to and exit from the constriction and, if appropriate, the flow velocity of the mixture through the constriction are measured, and the alcohol concentration is determined therefrom.

In this method, the fuel is alcohol. The alcohol is in particular methanol, ethanol, propanol or glycol. It is true that Published, Soviet Union Patent Application SU 1 789 909 A discloses a measuring device for measuring the viscosity of a liquid flowing through a pipeline, in particular of oil, in which a sample of the liquid is passed, parallel to the pipeline, through a capillary, and the flow velocity and pressure loss in the capillary are measured. From this, given the known geometry parameters, calculations can be used to determine the dynamic viscosity of the liquid. This measurement method is to be used to monitor the mixing process of products in particular in the oil industry. Even if SU 1 789 909 A states that other applications are possible as well as the oil industry, the document provides no more specific details of such applications. In particular, there is no indication of the application of determining the concentration of alcohols in the electrolyte of fuel cells.

The inventive application of the invention makes use of the surprising fact that the viscosity specifically of an alcohol/water mixture is highly dependent on the composition of the mixture, i.e. the viscosity changes with the alcohol content. For example, in the case of a methanol/water mixture the relative viscosity at 20° C. rises, with a methanol content increasing from 0–16% by mass (5 mol/l), from 1.0 to 1.5 (see in this respect the reference titled "CRC Handbook of Chemistry and Physics", 69th Edition 1988, page D-238).

The invention—during the determination of the alcohol concentration (in particular in the anode circuit of direct methanol fuel cells)—applies the Hagen-Poiseuille law. This law describes the relationship between the flow rate $dV/dt$ ($V$=Volume, $t$=time) of a fluid of viscosity $\eta$, for example a solution, through a type or flexible tube of length $L$ and radius $R$, on the one hand, and the pressure difference $\Delta p = p_1 - p_2$ between the entry to and exit from the pipe, on the other hand: $dV/dt = [\pi(p_1-p_2)R^4]/[8\eta L]$.

Therefore, in the method according to the invention, the anode liquid is pumped through a constriction of known dimensions ($L$, $R$) and the differential pressure between the entry to and exit from the constriction is measured; the pumping rate, i.e. the flow rate, is known. Then, the composition of the alcohol/water mixture is determined from the differential pressure, which is proportional to the viscosity. The particular advantage of the measurement method is that the measured variables pressure difference and—where required—flow velocity can be determined relatively accurately and without using complex and expensive equipment.

In the context of the present patent application, the term "constriction" is understood as meaning a line (pipe or flexible tube) of a defined length with an internal diameter that is smaller than the diameter of the actual line for the alcohol/water mixture. The constriction is advantageously a capillary, i.e. a constriction with a relatively narrow internal diameter, for example $\leq 3$ mm.

In accordance with an added mode of the invention, there are the steps of measuring a flow velocity of the alcohol/water mixture through the constriction; and using the flow velocity for determining a flow rate for assisting in determining the alcohol concentration.

In accordance with another mode of the invention, there is the step of using a direct methanol fuel cell as the fuel cell in which the alcohol/water mixed is used.

With the foregoing and other objects in view there is provided, in accordance with the invention, an apparatus. The apparatus contains a line having a constriction for transporting an alcohol/water mixture. The constriction has an entry and an exit. A delivery pump is disposed in the line for pumping the alcohol/water mixture. A device for measuring a differential pressure between the entry and the exit of the constriction is provided. The device uses the differential pressure for determining an alcohol concentration in the alcohol/water mixture.

In accordance with an added feature of the invention, the device further measures a flow velocity of the alcohol/water mixture for determining a flow rate for assisting in determining the alcohol concentration in the alcohol/water mixture.

In accordance with a further feature of the invention, the delivery pump is disposed upstream of the constriction.

In accordance with another feature of the invention, the line has a bypass, and the constriction and the device for measuring the differential pressure and the flow velocity are disposed in the bypass to the line for the alcohol/water mixture. In addition, it is preferred if the constriction is a capillary.

Other features which are considered as characteristic for the invention are set forth in the appended claims.

Although the invention is illustrated and described herein as embodied in a method and apparatus for determining an alcohol concentration in an alcohol/water mixture for fuel cells, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The single FIGURE of the drawing is a diagrammatic illustration of an apparatus for determining an alcohol concentration in an alcohol/water mixture for fuel cells according to the invention.

DESCRIPTION OF THE PREFERRED EMBODIMENTS

Referring now to the FIGURE of the drawing in detail, there is shown an apparatus for carrying out the method according to the invention. The apparatus has a line 1 with a bypass 2 and a constriction 3 disposed in the line 1 for delivering an alcohol/water mixture 4. A delivery pump 5 for pumping the mixture 4 is disposed in the line 1 and a device 6 for measuring a differential pressure between an entry to and an exit from the constriction 3 is provided. And, if appropriate, the device 6 also measures a flow velocity of the mixture 4. The device 6 is shown external to the line 1, but can be incorporated in the line 1 and is shown externally only for clarity. The delivery pump 5 is preferably disposed upstream of the constriction 3, but may also be fitted into the line 1 downstream of the constriction 3. The constriction 3 and the device 6 for measuring the differential pressure and the flow velocity are preferably disposed in the bypass 2 to the line 1 for the alcohol/water mixture 4. The bypass 2 of and by itself may also function as the constriction. However, the constriction 3 may be disposed in the line 1 itself and is shown by dashed lines in the FIGURE of the drawing.

An apparatus of this type has the advantage of being inexpensive to produce. Moreover, it can be small and compact, i.e. can be miniaturized.

In tests dealing with the way in which the method according to the invention is carried out, methanol/water mixtures of different concentrations were pumped at 25° C., with a constant pumping rate (flow rate), namely 120 ml/min, through a brass capillary with an internal diameter of 1.5 mm and a length of approximately 4 m; the pressure upstream and downstream of the capillary was measured. According to the Hagen-Poiseuille law, the pressure difference—at a constant pumping rate and with uniform capillary dimensions—is dependent only on the viscosity of the liquid. Since, in the concentration range that is of relevance to direct methanol fuel cells, the viscosity increases in (virtually) linear fashion as the methanol concentration rises, there is an unambiguous relationship between the pressure difference and the concentration. The unambiguous relationship was also confirmed in the tests carried out. Therefore, if a calibration curve is drawn up using solutions of known concentration, the unknown concentration of the methanol in the anode circuit can be determined by the pressure difference measured across the capillary.

There are two possible options for applying the apparatus.

First, the constriction 3 is fitted directly into an anode circuit, and the alcohol/water mixture 4 is forced through the constriction 3 by the circulation pump 5 that is already present and gives the value $dV/dt$ (flow rate). In this embodiment, however, all the mixture has to be transported through the constriction 3, which could entail an increased outlay on energy. Moreover, for example in the operation of DMFC-stacks, the methanol/water mixture is at a temperature in the range from 80 to 110° C., which could have an adverse effect on the viscosity differences.

Second, the constriction 3 is fitted into the bypass to the anode circuit. This has the advantage that only a small quantity of the alcohol/water mixture 4 has to be forced through the constriction 3. This small quantity, which has a lower heat capacity, can also, if necessary, be thermostatically controlled to low temperatures. However, in this embodiment an additional measurement of the flow rate (dV/dt) of the liquid has to take place in the bypass 2.

We claim:

1. A method for determining an alcohol concentration in an alcohol/water mixture of fuel cells operated with the alcohol/water mixture, which comprises the steps of:

pumping the alcohol/water mixture through a constriction;

measuring a differential pressure between an entry to and an exit from the constriction; and determining the alcohol concentration from the differential pressure.

2. The method according to claim 1, which comprises:

measuring a flow velocity of the alcohol/water mixture through the constriction; and using the flow velocity for determining a flow rate for assisting in determining the alcohol concentration.

3. The method according to claim 1, which comprises using a direct methanol fuel cell as the fuel cell in which the alcohol/water mixed is used.

4. An apparatus, comprising:

a line having a constriction for transporting an alcohol/water mixture, said constriction having an entry and an exit;

a delivery pump disposed in said line for pumping the alcohol/water mixture; and a device for measuring a differential pressure between said entry and said exit of said constriction, said device using the differential pressure for determining an alcohol concentration in the alcohol/water mixture.

5. The apparatus according to claim 4, wherein said device further measures a flow velocity of the alcohol/water mixture for determining a flow rate for assisting in determining the alcohol concentration in the alcohol/water mixture.

6. The apparatus according to claim 4, wherein said delivery pump is disposed upstream of said constriction.

7. The apparatus according to claim 4, wherein said line has a bypass, and said constriction and said device for measuring the differential pressure and the flow velocity are disposed in said bypass to said line for the alcohol/water mixture.

8. The apparatus according to claim 4, wherein said constriction is a capillary.

* * * * *